US006416992B1

(12) United States Patent
Mejza

(10) Patent No.: US 6,416,992 B1
(45) Date of Patent: Jul. 9, 2002

(54) COMPOSITIONS AND METHODS FOR PRODUCING RECOMBINANT ADENO-ASSOCIATED VIRUS

(75) Inventor: Stephen Mejza, Union City, CA (US)

(73) Assignee: Avigen, Inc., Alameda, CA (US)

( * ) Notice: Subject to any disclaimer, the term of this patent is extended or adjusted under 35 U.S.C. 154(b) by 0 days.

(21) Appl. No.: 09/417,418

(22) Filed: Oct. 13, 1999

(Under 37 CFR 1.47)

Related U.S. Application Data

(60) Provisional application No. 60/104,178, filed on Oct. 13, 1998.

(51) Int. Cl.[7] .................................................. C12N 7/02
(52) U.S. Cl. .......................... 435/239; 435/5; 435/69.1; 435/235.1; 435/320.1; 435/456; 435/457; 435/465; 435/476; 514/23.1; 514/23.5; 514/23.72
(58) Field of Search ..................... 435/5, 69.1, 235.1, 435/236, 239, 320.1, 456, 455, 457, 465, 476; 514/23.1, 23.5, 23.72; 935/23, 34

(56) References Cited

U.S. PATENT DOCUMENTS

| 5,173,414 A | | 12/1992 | Lebkowski et al. ....... 435/172.3 |
| 6,040,183 A | * | 3/2000 | Ferrari et al. ................ 435/457 |
| 6,194,191 B1 | * | 2/2001 | Zhang et al. ................ 435/239 |

FOREIGN PATENT DOCUMENTS

| EP | 0 488 528 A1 | 6/1992 |
| WO | WO 95/34670 | 12/1995 |
| WO | WO 97/06272 | 2/1997 |
| WO | WO 97/09441 | 3/1997 |
| WO | WO 97/17458 | 5/1997 |
| WO | WO 98/27207 | 6/1998 |

OTHER PUBLICATIONS

Graham Growth of 293 cells in suspension culture. Journal of General Virology (1987) pp. 937–940.*
Grimm et al., "Progress in Adeno–Associated Virus Type 2 Vector Production: Promises and Prospects for Clinical Use," *Human Gene Therapy* 10:2445–2450 (1999).
Ferrari et al., "New Developments in the Generation of Ad–Free, High–Titer rAAV Gene Therapy Vectors," *Nature Medicine* 3(11):1295–1297 (1997).
Grimm et al., "Novel Tools for Production and Purification of Recombinant Adenoassociated Virus Vectors," *Human Gene Therapy* 9:2745–2760 (1998).
Matsushita et al., "Adeno–Associated Virus Vectors Can be Efficiently Produced Without Helper Virus," *Gene Therapy* 5:938–945 (1998).
Salvetti et al., "Factors Influencing Recombinant Adeno–Associated Virus Production," *Human Gene Therapy* 9:695–706 (1998).
Xiao et al., "Production of High–Titer Recombinant Adeno–Associated Virus Vectors in the Absence of Helper Adenovirus," *Journal of Virology* 72(3):2224–2232.

* cited by examiner

*Primary Examiner*—Jeffrey Stucker
*Assistant Examiner*—Ulrike Winkler
(74) *Attorney, Agent, or Firm*—Robins & Pasternak LLP

(57) ABSTRACT

The present invention provides compositions and methods of producing recombinant AAV (rAAV) virions in large amounts or high titers. Also provided are methods for producing stably transformed host cells capable of producing rAAV virions.

8 Claims, No Drawings

SEQUENCE LISTING

<160> NUMBER OF SEQ ID NOS: 6

<210> SEQ ID NO 1
<211> LENGTH: 7
<212> TYPE: DNA
<213> ORGANISM: Artificial Sequence
<220> FEATURE:
<223> OTHER INFORMATION: Description of Artificial Sequence: AAV-2
      positions 255-261

<400> SEQUENCE: 1 tatttaa                                                            7

<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence: 5DIVE2

<400> SEQUENCE: 2
tgtggtcacg ctggggggggg gggcccgagt gagcacg                          37

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: EcoRV(1)

<400> SEQUENCE: 3
ccgctacagg gcgcgatatc agctcactca a                                 31

<210> SEQ ID NO 4
<211> LENGTH: 57
<212> TYPE: DNA
<213> ORGANISM: Artificial Sequence
<220> FEATURE:
<223> OTHER INFORMATION: Description of Artificial Sequence: EcoRV(2)

```
<400> SEQUENCE: 4
ggatccggta ccgcccgggc tctagaatcg atgtatacgt cgacgtttaa accatat          57

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: SrfI(1)

<400> SEQUENCE: 5
agaggcccgg gcgttttagg gcggagtaac ttgc                                   34

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: SrfI(2)

<400> SEQUENCE: 6
acatacccgc aggcgtagag ac                                                22
```

COMPOSITIONS AND METHODS FOR PRODUCING RECOMBINANT ADENO-ASSOCIATED VIRUS

CROSS-REFERENCE TO RELATED APPLICATION

This application is related to provisional patent application serial No. 60/104,178, filed Oct. 13, 1998, from which priority is claimed under 35 USC §119(e)(1) and which is incorporated herein by reference in its entirety.

TECHNICAL FIELD

The present invention relates generally to systems for use in adeno-associated virus (AAV) vector production. More specifically, the invention relates to methods of producing recombinant AAV virions in cells grown in suspension cultures, cells grown in suspension cultures and then adhered to a substrate or in cells grown in culture systems which are able to produce large amounts of virions.

BACKGROUND

Scientists are continually discovering genes that are associated with human diseases such as diabetes, hemophilia and cancer. Research efforts have also uncovered genes, such as erythropoietin (which increases red blood cell production), that are not associated with genetic disorders but code for proteins that can be used to treat numerous diseases. However, despite significant progress in the effort to identify and isolate genes, a major obstacle facing the biopharmaceutical industry is how to safely and persistently deliver effective quantities of the expression products of these genes to patients.

Currently, the protein products of these genes are synthesized in cultured bacterial, yeast, insect, mammalian, or other cells and delivered to patients by intravenous injection. While intravenous injection of recombinant proteins has been successful, it suffers from several drawbacks. First, patients often require one or more intravenous administrations in a single day in order to maintain the necessary levels of the protein in the blood stream. Even then, the level of protein is not maintained at physiological levels—the level of the protein is usually abnormally high immediately following injection and far below optimal levels prior to injection. Second, the cost of daily administrations for many diseases is often prohibitive, ranging in the hundreds of thousands of dollars a year. As a result, many patients must do without medicinal protein. Third, intravenous administration often does not deliver the protein to the target cells, tissues or organs in the body. And, if the protein reaches its target, it is often diluted to nontherapeutic levels. Finally, the daily intravenous administration is inconvenient and severely restricts the patient's lifestyle, especially when the patient is a child.

These shortcomings have led to the development of gene therapy methods for delivering sustained levels of specific proteins into patients. These methods allow clinicians to introduce a nucleic acid coding for a gene of interest directly into a patient (in vivo gene therapy) or into cells isolated from a patient or a donor, which are then returned to the patient (ex vivo gene therapy). The introduced nucleic acid then directs the patient's own cells or grafted cells to produce the desired protein product. Gene delivery, therefore, obviates the need for daily injections. Gene therapy will also allow clinicians to select specific organs or cellular targets (e.g., muscle, blood cells, brain cells, etc.) for therapy.

DNA may be introduced into a patient's cells in several ways. There are transfection methods including chemical methods, such as calcium phosphate precipitation and liposome-mediated transfection, and physical methods such as electroporation. In general, transfection methods are not suitable for in vivo gene delivery. There are also methods that use recombinant viruses. Current viral-mediated gene delivery methods employ retrovirus, adenovirus, herpes virus, pox virus, and adeno-associated virus vectors.

One of the more promising viral system that has been used for gene delivery is adeno-associated virus (AAV). AAV is a parvovirus which belongs to the genus Dependovirus. AAV has several attractive features not found in other viruses. First, AAV can infect a wide range of host cells, including nondividing cells. Second, AAV can infect cells from different species. Third, AAV has not been associated with any human or animal disease and does not appear to alter the biological properties of the host cell upon integration. Indeed, it is estimated that 80–85% of the human population has been exposed to the virus. Finally, AAV is stable at a wide range of physical and chemical conditions which lends itself to production, storage and transportation requirements.

The AAV genome is a linear, single-stranded DNA molecule containing about 4681 nucleotides. The AAV genome generally comprises an internal nonrepeating genome flanked on each end by inverted terminal repeats (ITRs). The ITRs are approximately 145 base pairs (bp) in length. The ITRs have multiple functions, including as origins of DNA replication, and as packaging signals for the viral genome.

The internal nonrepeated portion of the genome includes two large open reading frames, known as the AAV replication (rep) and capsid (cap) genes. The rep and cap genes code for viral proteins that allow the virus to replicate and package into a virion. In particular, a family of at least four viral proteins are expressed from the AAV rep region, Rep 78, Rep 68, Rep 52, and Rep 40, named according to their apparent molecular wight. The AAV cap region encodes at least three proteins, VPI, VP2, and VP3.

AAV is a helper-dependent virus; that is, it requires co-infection with a helper virus (e.g., adenovirus, herpesvirus or vaccinia), in order to form AAV virions. In the absence of co-infection with a helper virus, AAV establishes a latent state in which the viral genome inserts into a host cell chromosome, but infectious virions are not produced. Subsequent infection by a helper virus "rescues" the integrated genome, allowing it to replicate and package its genome into an infectious AAV virion. While AAV can infect cells from different species, the helper virus must be of the same species as the host cell. Thus, for example, human AAV will replicate in canine cells co-infected with a canine adenovirus.

AAV has been engineered to deliver genes of interest by deleting the internal nonrepeating portion of the AAV genome (i.e., rep and cap genes) and inserting a heterologous gene between the ITRs. The heterologous gene is typically functionally linked to a heterologous promoter (constitutive, cell-specific, or inducible) capable of driving gene expression in the patient's target cells under appropriate conditions. Termination signals, such as polyadenylation sites, can also be included.

To produce infectious rAAV virus containing the heterologous gene, a suitable producer cell line is transfected with a rAAV vector containing a heterologous gene. The producer cell is concurrently transfected with a second plasmid harboring the AAV rep and cap genes under the control of their respective endogenous promoters or heterologous promoters. Finally, the producer cell is infected with a helper virus, such as adenovirus, or helper virus genes, such as the adenovirus E1, E2A, E4 and VA RNA genes (WO 97/17458).

Once these factors come together, the heterologous gene is replicated and packaged as though it were a wild-type AAV genome. When a patient's cells are infected with the resulting rAAV virions, the heterologous gene enters and is expressed in the patient's cells. Because the patient's cells lack the rep and cap genes and the adenovirus helper genes, the rAAV cannot further replicate and package. Similarly, wild-type AAV cannot be formed.

Despite the promise of rAAV as a gene therapy tool, one of the shortcomings of the currently available technology is the inability to produce commercial scale viral titers.

Currently, high titer AAV virions are made by simultaneously transfecting a monolayer of producer cells (typically 293 cells) with an AAV vector and an AAV helper vector carrying the rep and cap genes using conventional transfection reagents (e.g., calcium phosphate) followed by infection with live adenovirus. Current protocols perform transfections in 10 cm plates (see, e.g., U.S. Pat. No. 5,173,414). Typically, in order to have a successful transfection, the monolayer must not be confluent. Alternatively, the production cell line is simultaneously transfected with an AAV vector, an AAV helper vector, and an adenoviral helper vector carrying the E1, E2A, E4, and VA RNA.

While this method produces sufficiently high titers for most applications, it is insufficient for commercial-scale production of AAV virions. A method is needed by which large-scale production of AAV virions can be achieved.

SUMMARY

Accordingly, it is a primary object of the invention to provide a method that addresses the aforementioned need in the art.

It is another object of the invention to provide a method for producing large-scale, high titer recombinant AAV (rAAV) virions comprising providing a culture of cells and transfecting the cells with a rAAV construct under conditions that permit the formation of rAAV virions. Optionally, the cells are grown in large-scale culture containers (e.g., roller bottles, large flasks, etc). The cells may also be grown in suspension or grown in suspension and adhered to a substrate, such as a fibrous disk, prior to transfection.

It is yet another object of the invention to provide a method for producing a stably transformed host cell capable of producing rAAV virions.

In one embodiment, a method for large-scale production of rAAV virions is provided. The method comprises providing a population of cells, admixing a first polynucleotide comprising an AAV vector, a second polynucleotide comprising an AAV helper construct, and a third polynucleotide comprising an accessory function vector, with at least one transfection reagent to provide polynucleotide:transfection reagent complexes, transfecting the cells with the polynucleotide:transfection reagent complexes to provide transfected cells, culturing the transfected cells under conditions that permit the formation of rAAV virions, and harvesting the rAAV virions. The population of cells can be grown in suspension cultures or grown in suspension cultures and then subsequently adhered to a substrate, such as a fibrous substrate, prior to transfection. Alternatively, the cells are grown in large-scale culture containers.

In another embodiment of the invention, a method of producing rAAV is provided in which the aforementioned first and second polynucleotides are admixed with at least one transfection reagent to form polynucleotide:transfection reagent complexes which are then used to transfect the cells. Either concurrently with or subsequent to transfecting the cells with the complexes, the cells are infected with an AAV helper virus. The infected cells are then cultured as above and the rAAV virions thus produced are harvested.

In yet another embodiment a method is provided for producing a stably transformed host cell capable of producing rAAV virions. The method comprises providing a population of cells, admixing a first polynucleotide comprising an AAV vector, a second polynucleotide comprising an AAV helper construct, and a third polynucleotide comprising an accessory function vector, with at least one transfection reagent to provide polynucleotide:transfection reagent complexes, transfecting the cells with the polynucleotide:transfection reagent complexes to provide transfected cells, and culturing the transfected cells under conditions that permit the integration of the first polynucleotide, the second polynucleotide, and the third polynucleotides, or a combination thereof, into the host cell genome. The cell populations are typically capable of growth in suspension culture or are grown in large-scale culture containers.

In still another embodiment a method is provided for producing a stably transformed host cell capable of producing rAAV virions. The method comprises providing a population of cells as described above, admixing a first polynucleotide comprising an AAV vector and a second polynucleotide comprising an AAV helper construct with at least one transfection reagent to provide polynucleotide:transfection reagent complexes, transfecting the cells with the polynucleotide:transfection reagent complexes, infecting the cells with an AAV helper virus, and culturing the infected cells under conditions that permit the integration of the first polynucleotide, the second polynucleotide, the AAV helper virus, or a combination thereof, into the host cell genome.

These and other embodiments of the subject invention will readily occur to those of ordinary skill in the art in view of the disclosure herein.

DETAILED DESCRIPTION OF THE INVENTION

The practice of the present invention will employ, unless otherwise indicated, conventional methods of virology, microbiology, molecular biology and recombinant DNA techniques within the skill of the art. Such techniques are explained filly in the literature. See, e.g., Sambrook et al. *Molecular Cloning: A Laboratory Manual* (Current Edition); *DNA Cloning: A Practical Approach*, Vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition); *CRC Handbook of Parvoviruses*, vol. I & II (P. Tijssen, ed.); *Fundamental Virology*, 2nd Edition, vol. I & II (B. N. Fields and D. M. Knipe, eds.); Freshney *Culture of Animal Cells, A Manual of Basic Technique* (Wiley-Liss, Third Edition); and Ausubel et al. (1991) *Current Protocols in Molecular Biology* (Wiley Interscience, NY).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

A. Definitions

In describing the present invention, the following terms will be employed, and are intended to be defined as indicated below.

By "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

By an "AAV vector" is meant a vector derived from an adeno-associated virus serotype, including without limitation, AAV-1, AAV-2, AAV-3, AAV-4, AAV-5, AAVX7, etc. AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging.

"AAV helper functions" refer to AAV-derived coding sequences which can be expressed to provide AAV gene products that, in turn, function in trans for productive AAV replication. Thus, AAV helper functions include both of the major AAV open reading frames (ORFs), rep and cap. The Rep expression products have been shown to possess many functions, including, among others: recognition, binding and nicking of the AAV origin of DNA replication; DNA helicase activity; and modulation of transcription from AAV (or other heterologous) promoters. The Cap expression products supply necessary packaging functions. AAV helper functions are used herein to complement AAV functions in trans that are missing from AAV vectors.

The term "AAV helper construct" refers generally to a nucleic acid molecule that includes nucleotide sequences providing AAV functions deleted from an AAV vector which is to be used to produce a transducing vector for delivery of a nucleotide sequence of interest. AAV helper constructs are commonly used to provide transient expression of AAV rep and/or cap genes to complement missing AAV functions that are necessary for lytic AAV replication; however, helper constructs lack AAV ITRs and can neither replicate nor package themselves. AAV helper constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) *J. Virol.* 63:3822–3828; and McCarty et al. (1991) *J. Virol.* 65:2936–2945. A number of other vectors have been described which encode Rep and/or Cap expression products. See, e.g., U.S. Pat. No. 5,139,941.

The term "accessory functions" refers to non-AAV derived viral and/or cellular functions upon which AAV is dependent for its replication. Thus, the term captures proteins and RNAs that are required in AAV replication, including those moieties involved in activation of AAV gene transcription, stage specific AAV mRNA splicing, AAV DNA replication, synthesis of Cap expression products and AAV capsid assembly. Viral-based accessory functions can be derived from any of the known helper viruses such as adenovirus, herpesvirus (other than herpes simplex virus type-1) and vaccinia virus.

For example, adenovirus-derived accessory functions have been widely studied, and a number of adenovirus genes involved in accessory functions have been identified and partially characterized. See, e.g., Carter, B. J. (1990) "Adeno-Associated Virus Helper Functions," in *CRC Handbook of Parvoviruses*, vol. I (P. Tijssen, ed.), and Muzyczka, N. (1992) *Curr. Topics. Microbiol. and Immun.* 158:97–129. Specifically, early adenoviral gene regions E1a, E2a, E4, VAI RNA and, possibly, E1b are thought to participate in the accessory process. Janik et al. (1981) *Proc. Natl. Acad. Sci. USA* 78:1925–1929. Herpesvirus-derived accessory functions have been described. See, e.g., Young et al. (1979) *Prog. Med. Virol.* 25:113. Vaccinia virus-derived accessory functions have also been described. See, e.g., Carter, B. J. (1990), supra., Schlehofer et al. (1986) *Virology* 152:110–117.

The term "accessory function vector" refers generally to a nucleic acid molecule that includes nucleotide sequences providing accessory functions. An accessory function vector can be transfected into a suitable host cell, wherein the vector is then capable of supporting AAV virion production in the host cell. Expressly excluded from the term are infectious viral particles as they exist in nature, such as adenovirus, herpesvirus or vaccinia virus particles. Thus, accessory function vectors can be in the form of a plasmid, phage, transposon or cosmid.

By "capable of supporting efficient rAAV virion production" is meant the ability of an accessory function vector or system to provide accessory functions that are sufficient to complement rAAV virion production in a particular host cell at a level substantially equivalent to or greater than that which could be obtained upon infection of the host cell with an adenovirus helper virus. Thus, the ability of an accessory function vector or system to support efficient rAAV virion production can be determined by comparing rAAV virion titers obtained using the accessory vector or system with titers obtained using infection with an infectious adenovirus. More particularly, an accessory function vector or system supports efficient rAAV virion production substantially equivalent to, or greater than, that obtained using an infectious adenovirus when the amount of virions obtained from an equivalent number of host cells is not more than about 200 fold less than the amount obtained using adenovirus infection, more preferably not more than about 100 fold less, and most preferably equal to, or greater than, the amount obtained using adenovirus infection.

By "recombinant virus" is meant a virus that has been genetically altered, e.g., by the addition or insertion of a heterologous nucleic acid construct into the particle.

By "AAV virion" is meant a complete virus particle, such as a wild-type (wt) AAV virus particle (comprising a linear, single-stranded AAV nucleic acid genome associated with an AAV capsid protein coat). In this regard, single-stranded AAV nucleic acid molecules of either complementary sense, e.g., "sense" or "antisense" strands, can be packaged into any one AAV virion and both strands are equally infectious.

A "recombinant AAV virion," or "rAAV virion" is defined herein as an infectious, replication-defective virus composed of an AAV protein shell, encapsidating a heterologous nucleotide sequence of interest which is flanked on both sides by AAV ITRs. A rAAV virion is produced in a suitable host cell which has had an AAV vector, AAV helper functions and accessory functions introduced therein. In this manner, the host cell is rendered capable of encoding AAV polypeptides that are required for packaging the AAV vector (containing a recombinant nucleotide sequence of interest) into infectious recombinant virion particles for subsequent gene delivery.

The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) *Virology*, 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA moieties, such as a nucleotide integration vector and other nucleic acid molecules, into suitable host cells.

The term "host cell" denotes, for example, microorganisms, yeast cells, insect cells, and mammalian cells, that can be, or have been, used as recipients of an AAV helper construct, an AAV vector plasmid, an accessory function vector, or other transfer DNA. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

A "coding sequence" or a sequence which "encodes" a particular protein, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the coding sequence.

A "nucleic acid" sequence refers to a DNA or RNA sequence. The term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters".

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

By "isolated" when referring to a nucleotide sequence, is meant that the indicated molecule is present in the substantial absence of other biological macromolecules of the same type. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

For the purpose of describing the relative position of nucleotide sequences in a particular nucleic acid molecule throughout the instant application, such as when a particular nucleotide sequence is described as being situated "upstream," "downstream," "3'," or "5'" relative to another sequence, it is to be understood that it is the position of the sequences in the "sense" or "coding" strand of a DNA molecule that is being referred to as is conventional in the art.

"Homology" refers to the percent identity between two polynucleotide or two polypeptide moieties. The correspondence between the sequence from one moiety to another can be determined by techniques known in the art. For example, homology can be determined by a direct comparison of the sequence information between two polypeptide molecules by aligning the sequence information and using readily available computer programs such as ALIGN, Dayhoff, M. O. (1978) in *Atlas of Protein Sequence and Structure* 5:Suppl. 3, National biomedical Research Foundation, Washington, D.C. Preferably, default parameters are used for alignment. One alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST.

Alternatively, homology can be determined by hybridization of polynucleotides under conditions which form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80%–85%, preferably at least about 90%, and most preferably at least about 95%–98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

A "functional homologue," or a "functional equivalent" of a given polypeptide includes molecules derived from the native polypeptide sequence, as well as recombinantly produced or chemically synthesized polypeptides which function in a manner similar to the reference molecule to achieve a desired result. Thus, a functional homologue of AAV Rep68 or Rep78 encompasses derivatives and analogues of those polypeptides—including any single or multiple amino acid additions, substitutions and/or deletions occurring internally or at the amino or carboxy termini thereof—so long as integration activity remains.

A "functional homologue," or a "functional equivalent" of a given adenoviral nucleotide region includes similar regions derived from a heterologous adenovirus serotype, nucleotide regions derived from another virus or from a cellular source, as well as recombinantly produced or chemically synthesized polynucleotides which function in a manner similar to the reference nucleotide region to achieve a desired result. Thus, a functional homologue of an adenoviral VA RNA gene region or an adenoviral E2a gene region encompasses derivatives and analogues of such gene regions—including any single or multiple nucleotide base additions, substitutions and/or deletions occurring within the regions, so long as the homologue retains the ability to provide its inherent accessory function to support AAV virion production at levels detectable above background.

For the purpose of describing the relative position of nucleotide sequences in a particular nucleic acid molecule throughout the instant application, such as when a particular nucleotide sequence is described as being situated "upstream," "downstream," "3'" or "5'" relative to another sequence, it is to be understood that it is the position of the sequences in the "sense" or "coding" strand of a DNA molecule that is being referred to as is conventional in the art.

By "suspension" or "suspension culture" is meant a cell culture maintained in a liquid. Although not required, suspension cultures are frequently maintained in suspension by stirring or shaking or other means of agitation. The term "adherent culture" refers to cells that are maintained adhered to a substrate. "Large-scale production" or "commercial-scale production" refers to processes which allow for the generation of large amounts of the desired product as compared to standard protocols. It is to be understood that large amounts of rAAV virions can mean higher titers or higher numbers of virions as compared to those produced using standard procedures. Currently, standard procedures yield approximately $10^{14}$ AAV particles from transfection of many small-volume culture dishes (e.g., 100 mm plates having a surface area of about 55 cm$^2$). The present invention makes use of large volume culture containers (e.g., containers such as those described below having a surface area greater than about 150 cm$^2$) to produce at least $10^{14}$ AAV particles per batch, preferably between about $10^{15}$ and $10^{17}$ AAV particles per batch. Thus, in the context of the present invention, large-scale production refers to production of more, or higher titers of, rAAV virions as compared to amounts or titers produced using standard culture conditions. Unlike standard procedures, the present invention allows for large-scale production of rAAV virions, for example, from suspension cultures, from suspension cultures where the cells are subsequently adhered to a substrate or from cells grown in culture containers that are larger than the standard cell culture containers. Non-limiting examples of large-volume culture containers suitable for use in the present invention include roller bottles (surface area from about 490 cm$^2$ to about 1750 cm$^2$), expanded roller bottles (surface area about 1700 cm$^2$), flasks (growth area from about 150 cm$^2$ to about 225 cm$^2$), fermentation flasks (volume between about 3 and 100 liters) or any other container that allows for production of significantly more product than the standard culture containers. Suitable culture containers can be obtained from a variety of commercial sources, for example Corning Costar, Corning, N.Y.

As used herein the term "substrate" or "support" refers to the surface or material on which cells will grow. Cells adhered to a substrate may be entrapped within the substrate, may adhere to the surface of the substrate or some cells may be entrapped and some may adhere to the surface. There are a wide variety of suitable substrates, including, but not limited to, fibrous materials, both natural and synthetic (e.g., nitrocellulose, cotton, silk, other woven, spun or felted fabrics), glass, other polymeric materials (e.g., polyethylene terephthalate, polyglygolic acid, polylactic acid.

B. General Methods

The present invention provides for the successful transfection of cells in suspension culture and suspension cultures adhered to substrate to produce rAAV virions. Thus, the method allows for the large-scale production of recombinant AAV virions. The method comprises admixing a population of cells in large-scale culture with polynucleotide:transfection reagent complexes wherein the polynucleotide is in the form of a first polynucleotide comprising an AAV expression vector, a second polynucleotide comprising an AAV helper construct, and a third polynucleotide comprising an accessory function vector. The first, second and third polynucleotides, or combinations thereof, can be on the same or different polynucleotides or plasmids. The large-scale culture systems can be, for example, suspension cultures, suspension cultures which are subsequently adhered to a substrate or large culture containers such as roller bottles, T-225 flasks, etc. The transfected cells are then grown under conditions that permit the production of rAAV virions, which are then harvested.

Alternatively, the cells can be transfected with a preformed polynucleotide:transfection reagent complex wherein the polynucleotide comprises the aforementioned first and second polynucleotides. As above, the first and second polynucleotides can be on the same or different polynucleotides or plasmids. Either concurrently with or subsequent to transfecting the cells with the complexes, the cells are infected with an AAV helper virus. The infected cells are then cultured as above (e.g., in suspension, suspension followed by substrate adherence or large flasks) and the rAAV virions thus produced are harvested.

The transfection reagent may be selected from transfection reagents well known in the art that are capable of promoting transfection of cells grown in suspension culture. Examples of transfection reagents include calcium phosphate, strontium phosphate, polycationic polymers, e.g., Superfect (QIAGEN®), liposomes, and polyethyleneimine (PEI). A preferred transfection reagent is polyethyleneimine. Thus, transfection may be effected using any technique well known in the art, including but not limited to electroporation and lipid-mediated transfection.

1. AAV Expression Vectors

AAV expression vectors are constructed using known techniques to at least provide as operatively linked components in the direction of transcription, control elements including a transcriptional initiation region, the DNA of interest and a transcriptional termination region. The control elements are selected to be functional in a mammalian muscle cell. The resulting construct which contains the operatively linked components is bounded (5' and 3') with functional AAV ITR sequences.

The nucleotide sequences of AAV ITR regions are known. See, e.g., Kotin, R. M. (1994) *Human Gene Therapy* 5:793–801; Berns, K. I. "Parvoviridae and their Replication" in *Fundamental Virology*, 2nd Edition, (B. N. Fields and D. M. Knipe, eds.) for the AAV-2 sequence. AAV ITRs used in the vectors of the invention need not have a wild-type nucleotide sequence, and may be altered, e.g., by the insertion, deletion or substitution of nucleotides. Additionally, AAV ITRs may be derived from any of several AAV serotypes, including without limitation, AAV-1, AAV-2, AAV-3, AAV-4, AAV-5, AAVX7, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

Suitable DNA molecules for use in AAV vectors will be less than about 5 kilobases (kb) in size and will include, for example, a gene that encodes a protein that is defective or missing from a recipient subject or a gene that encodes a protein having a desired biological or therapeutic effect (e.g., an antibacterial, antiviral or antitumor function).

Suitable DNA molecules include, but are not limited to, those encoding for proteins used for the treatment of endocrine, metabolic, hematologic, cardiovascular, neurologic, musculoskeletal, urologic, pulmonary and immune disorders, including such disorders as inflammatory diseases, autoimmune, chronic and infectious diseases, such as AIDS, cancer, hypercholestemia, insulin disorders such as diabetes, growth disorders, various blood disorders including various anemias, thalassemias and hemophilia; genetic defects such as cystic fibrosis, Gaucher's Disease, Hurler's Disease, adenosine deaminase (ADA) deficiency, emphysema, or the like.

The selected nucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

The AAV expression vector which harbors the DNA molecule of interest bounded by AAV ITRs, can be constructed by directly inserting the selected sequence(s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173,414 and 5,139,941; International Publication Nos. WO 92/01070 (published Jan. 23, 1992) and WO 93/03769 (published Mar. 4, 1993); Lebkowski et al. (1988) *Molec. Cell. Biol.* 8:3988–3996; Vincent et al. (1990) *Vaccines* 90 (Cold Spring Harbor Laboratory Press); Carter (1992) *Current Opinion in Biotechnology* 3:533–539; Muzyczka (1992) *Current Topics in Microbiol. and Immunol.* 158:97–129; Kotin (1994) *Human Gene Therapy* 5:793–801; Shelling and Smith (1994) *Gene Therapy* 1:165–169; and Zhou et al. (1994) *J. Exp. Med.* 179:1867–1875.

Alternatively, AAV ITRs can be excised from the viral genome or from an AAV vector containing the same and fused 5' and 3' of a selected nucleic acid construct that is present in another vector using standard ligation techniques, such as those described in Sambrook et al., supra. For example, ligations can be accomplished in 20 mM Tris-Cl pH 7.5, 10 mM $MgCl_2$, 10 mM DTT, 33 μg/ml BSA, 10 mM–50 mM NaCl, and either 40 μM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 30–100 μg/ml total DNA concentrations (5–100 nM total end concentration). AAV vectors which contain ITRs have been described in, e.g., U.S. Pat. No. 5,139,941. In particular, several AAV vectors are described therein which are available from the American Type Culture Collection ("ATCC") under Accession Numbers 53222, 53223, 53224, 53225 and 53226.

Additionally, chimeric genes can be produced synthetically to include AAV ITR sequences arranged 5' and 3' of one or more selected nucleic acid sequences. Preferred codons for expression of the chimeric gene sequence in mammalian muscle cells can be used. The complete chimeric sequence is assembled from overlapping oligonucleotides prepared by standard methods. See, e.g., Edge (1981) *Nature* 292:756; Nambair et al. (1984) *Science* 223:1299; Jay et al. (1984) *J. Biol. Chem.* (1984) 259:6311.

For the purposes of the invention, suitable host cells for producing rAAV virions include microorganisms, yeast cells, insect cells, and mammalian cells, that can be, or have been, used as recipients of a heterologous DNA molecule and that are capable of growth in suspension culture. The term includes the progeny of the original cell which has been transfected. Thus, a "host cell" as used herein generally refers to a cell which has been transfected with an exogenous DNA sequence. Cells from the stable human cell line, 293 (readily available through, e.g., the American Type Culture Collection under Accession Number ATCC CRL1 573) are preferred in the practice of the present invention. Particularly, the human cell line 293 is a human embryonic kidney cell line that has been transformed with adenovirus type-5 DNA fragments (Graham et al. (1977) *J. Gen. Virol.* 36:59), and expresses the adenoviral E1a and E1b genes (Aiello et al. (1979) *Virology* 94:460). The 293 cell line is readily transfected, and provides a particularly convenient platform in which to produce rAAV virions.

2. AAV Helper Functions

Host cells containing the above-described AAV expression vectors must be rendered capable of providing AAV helper functions in order to replicate and encapsidate the nucleotide sequences flanked by the AAV ITRs to produce rAAV virions. AAV helper functions are generally AAV-derived coding sequences which can be expressed to provide AAV gene products that, in turn, function in trans for productive AAV replication. AAV helper functions are used herein to complement necessary AAV functions that are missing from the AAV expression vectors. Thus, AAV helper functions include one, or both of the major AAV ORFs, namely the rep and cap coding regions, or functional homologues thereof.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. For a description of the AAV rep coding region, see, e.g., Muzyczka, N. (1992) *Current Topics in Microbiol. and Immunol.* 158:97–129; and Kotin, R. M. (1994) *Human Gene Therapy* 5:793–801. Suitable homologues of the AAV rep coding region include the human herpesvirus 6 (HHV-6) rep gene which is also known to mediate AAV-2 DNA replication (Thomson et al. (1994) *Virology* 204:304–311).

By "AAV cap coding region" is meant the art-recognized region of the AAV genome which encodes the capsid proteins VP1, VP2, and VP3, or functional homologues thereof. These Cap expression products supply the packaging functions which are collectively required for packaging the viral genome. For a description of the AAV cap coding region, see, e.g., Muzyczka, N. and Kotin, R. M. (supra).

AAV helper functions are introduced into the host cell by transfecting the host cell with an AAV helper construct either prior to, or concurrently with, the transfection of the AAV expression vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves.

These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) *J. Virol.* 63:3822–3828; and McCarty et al. (1991) *J. Virol.* 65:2936–2945. A number of other vectors have been described which encode Rep and/or Cap expression products. See, e.g., U.S. Pat. No. 5,139,941.

Both AAV expression vectors and AAV helper constructs can be constructed to contain one or more optional selectable markers. Suitable markers include genes which confer antibiotic resistance or sensitivity to, impart color to, or change the antigenic characteristics of those cells which have been transfected with a nucleic acid construct containing the selectable marker when the cells are grown in an appropriate selective medium. Several selectable marker genes that are useful in the practice of the invention include the hygromycin B resistance gene (encoding Aminoglycoside phosphotranferase (APH)) that allows selection in mammalian cells by conferring resistance to G418 (available from Sigma, St. Louis, Mo.). Other suitable markers are known to those of skill in the art.

3. AAV Accessory Functions

The host cell (or packaging cell) must also be rendered capable of providing nonAAV-derived functions, or "accessory functions," in order to produce rAAV virions. Accessory functions are nonAAV-derived viral and/or cellular functions upon which AAV is dependent for its replication. Thus, accessory functions include at least those nonAAV proteins and RNAs that are required in AAV replication, including those involved in activation of AAV gene transcription, stage specific AAV mRNA splicing, AAV DNA replication, synthesis of Cap expression products and AAV capsid assembly. Viral-based accessory functions can be derived from any of the known helper viruses.

In particular, accessory functions can be introduced into and then expressed in host cells using methods known to those of skill in the art. Typically, accessory functions are provided by infection of the host cells with an unrelated helper virus. A number of suitable helper viruses are known, including adenoviruses; herpesviruses such as herpes simplex virus types 1 and 2; and vaccinia viruses. Nonviral accessory functions will also find use herein, such as those provided by cell synchronization using any of various known agents. See, e.g., Buller et al. (1981) *J. Virol.* 40:241–247; McPherson et al. (1985) *Virology* 147:217–222; Schlehofer et al. (1986) *Virology* 152:110–117.

Alternatively, accessory functions can be provided using an accessory function vector. Accessory function vectors include nucleotide sequences that provide one or more accessory functions. An accessory function vector is capable of being introduced into a suitable host cell in order to support efficient AAV virion production in the host cell. Accessory function vectors can be in the form of a plasmid, phage, transposon or cosmid. Accessory vectors can also be in the form of one or more linearized DNA or RNA fragments which, when associated with the appropriate control elements and enzymes, can be transcribed or expressed in a host cell to provide accessory functions.

Nucleic acid sequences providing the accessory functions can be obtained from natural sources, such as from the genome of an adenovirus particle, or constructed using recombinant or synthetic methods known in the art. In this regard, adenovirus-derived accessory functions have been widely studied, and a number of adenovirus genes involved in accessory functions have been identified and partially characterized. See, e.g., Carter (1990) "Adeno-Associated Virus Helper Functions," in CRC Handbook of Parvoviruses, vol. I (P. Tijssen, ed.), and Muzyczka (1992) Curr. Topics. Microbiol. and Immun. 158:97–129. Specifically, early adenoviral gene regions E1a, E2a, E4, VA RNA and, possibly, E1b are thought to participate in the accessory process. Janik et al. (1981) Proc. Natl. Acad. Sci. USA 78:1925–1929. Herpesvirus-derived accessory functions have been described. See, e.g., Young et al. (1979) Prog. Med. Virol. 25:113. Vaccinia virus-derived accessory functions have also been described. See, e.g., Carter, B. J. (1990), supra., Schlehofer et al. (1986) Virology 152:110–117.

As a consequence of the infection of the host cell with a helper virus, or transfection of the host cell with an accessory function vector, accessory functions are expressed which transactivate the AAV helper construct to produce AAV Rep and/or Cap proteins. The Rep expression products excise the recombinant DNA (including the DNA of interest) from the AAV expression vector. The Rep proteins also serve to duplicate the AAV genome. The expressed Cap proteins assemble into capsids, and the recombinant AAV genome is packaged into the capsids. Thus, productive AAV replication ensues, and the DNA is packaged into rAAV virions.

Following recombinant AAV replication, rAAV virions can be purified from the host cell using a variety of conventional purification methods, such as CsCl gradients. Further, if infection is employed to express the accessory functions, residual helper virus can be inactivated, using known methods. For example, adenovirus can be inactivated by heating to temperatures of approximately 60° C. for, e.g., 20 minutes or more. This treatment effectively inactivates only the helper virus since AAV is extremely heat stable while the helper adenovirus is heat labile.

The resulting rAAV virions containing the heterologous nucleotide sequence of interest can then be used for gene delivery, such as in gene therapy applications, for the production of transgenic animals, in vaccination, ribozyme and antisense therapy, as well as for the delivery of genes in vitro, to a variety of cell types.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

MATERIALS AND METHODS

Suspension Cell Culture

Cells from the stable human cell line, 293, a human embryonic kidney cell line that has been transformed with adenovirus type-5 DNA fragments (ATCC Accession Number ATCC CRL1573), see U.S. Pat. No. 5,622,856 to Natsoulis ("the '856 patent") were grown in S-Medium (DMEM without calcium, 5% fetal calf serum), 4 mM glutamine, 110 mg/L sodium pyruvate and, optionally, pluronic F68 (Gibco/BRL Cat. No. 2404-032) at 50–100 rpm in spinner flasks in a 37° C. incubator with a 95% $O_2$:5%$CO_2$. Cells were grown for at least 5 passages and are referred to as 293-S cells.

Attachment to Disks

Suspension cell cultures were attached to fibrous disks (e.g., Fibra-Cel disks, New Brunswick Scientific, Edison, N.J.). Fibrous disks were sterilized by autoclaving in phosphate buffered saline. Seventy-one fibrous disks were added to a spinner flask containing 100 mls of a rapidly growing 293S cell culture ($2.5 \times 10^6$ cells/ml). After the addition of 100 µl of 1.8M $CaCl_2$, the flask was agitated for 3 minutes (30 rpm) and then the mixture of disks and cells were left to settle. Disks (approximately 20) were removed at 15, 30, 60, and 120 minutes after the initial settling and the culture was agitated (3 minutes, 30 rpm) after each disk removal time point. Each group of disks were placed in 10 cm dishes containing 10 ml of calcium DMEM (10% fetal bovine serum) and incubated overnight.

Vectors Constructs

A. Construction of pAAVLacZ

An AAV vector carrying the lacZ gene (pAAV-lacZ) was constructed as follows. The AAV coding region of pSub201 (Samulski et al. (1987) J. Virol 61:3096–3101), between the XbaI sites, was replaced with EcoRI linkers, resulting in plasmid pAS203. The EcoRI to HindIII fragment of pCMVβ (CLONETECH) was rendered blunt ended and cloned in the Klenow treated EcoRI site of pAS203 to yield pAAV-lacZ.

B. Construction of pHelp 19

The AAV helper construct pHelp 19, which is capable of expressing the AAV Rep and Cap polypeptide products includes an approximately 4.8 Kb nucleotide stretch comprising an AAV rep and cap coding region and a downstream AAV P5 promoter that are interposed between two FRT sites. This plasmid is the same as the pGN1909 described in the '856 patent, supra, except that the TATA box of the downstream P5 promoter (AAV-2 positions 255–261, sequence TATTTAA (SEQ ID NO:1)) was eliminated by changing the sequence to GGGGGGG using the mutagenic oligonucleotide 5DIVE2 (5'-TGT GGT CAC GCT GGG GGG GGG GGC CCG AGT GAG CAC G-3')(SEQ ID NO:2). The resulting construct, pH19, is 7328 bp in length.

C. Construction of Pladeno 5

Pladeno 5 is a plasmid that provides a complete set of adenovirus helper functions for AAV vector production when transfected into 293 cells. Essentially, Pladeno 5 is composed of the E2A, E4, and VA RNA regions from adenovirus-2 and a plasmid back bone. The Pladeno 5 plasmid was made in two steps.

Step 1: Construction of the assembly plasmid—pBSIIs/k+ was modified to replace the 637 bp region encoding the polylinker and alpha complementation cassette with a single EcoRV site using oligonucleotide directed mutagenesis and the oligonucleotide 5'-CCG CTA CAG GGC GCG ATA TCA GCT CAC TCA A-3' (SEQ ID NO:3). A polylinker encoding the restriction sites BamHI, KpnI, SrfI, XbaI, ClaI, Bst11071, SalI, PmeI and NdeI was then cloned into the EcoRV site (5'-GGA TCC GGT ACC GCC CGG GCT CTA GAA TCG ATG TAT ACG TCG ACG TTT AAA CCA TAT G-3')(SEQ ID NO:4).

Step 2: Installation of the E2A, VA RNA, and E4 regions—Adenovirus-2 DNA was digested and restriction fragments encoding the E2A region (a 5,335 bp, KpnI-SrfI fragment corresponding to positions 22,233–27,568 of the adenovirus-2 genome) and the VA RNAs (a 731 bp, EcoRV-SacII fragment corresponding to positions 10,426–11,157 of the adenovirus-2 genome) were isolated. The E2A fragment was installed between the SalI and KpnI sites of the polylinker. An E4 region was first assembled in pBSIIs/k+ by ligating a 13,864 bp, BamHI-AvrII fragment corresponding to adenovirus-2 positions 21,606–35,470 (encoding the 5' end of the gene) and a 462 bp, AvrII and SrfI, digested PCR fragment corresponding to adenovirus-2 positions 35,371–35,833 (encoding the 3' end of the gene) between the BamHI and SmaI sites of pBSIIs/k+. The oligonucleotides used to produce the PCR fragment were designed to introduce a SrfI site at the junction were the E4 promoter and the adenovirus terminal repeat intersect and have the sequences 5'-AGA GGC CCG GGC GTT TTA GGG CGG AGT AAC TTG C-3' (SEQ ID NO:5) and 5'-ACA TAC CCG CAG GCG TAG AGA C-3' (SEQ D NO:6). The intact E4 region was excised by cleavage with SrfI and SpeI and the 3,189 bp fragment corresponding to adenovirus-2 positions 32,644–35,833 was cloned into the E2A intermediate between the SrfI and XbaI sites. Finally, the VA RNA fragment was inserted into the Bst1107 site after T4 polymerase-mediated blunt end modification of the SacII site. The genes in Pladeno 5 are arranged such that the 5' ends of the E2A and E4 promoters abut, causing the regions to transcribe away from each other in opposite directions. The VA RNA genes, which are located at the 3' end of the E4 gene, transcribe towards the E4 gene. The plasmid is 11,619 bp in length.

Transfection Reagents

A. Calcium Phosphate

Approximately 10–40 µg of DNA is added to 1.2 mLs of 0.3 M of $CaCl_2$ followed by the addition of an equal volume of 2×HBS (280 mM NaCl, 50 mM Hepes, 1.5 mM $Na_2PO_4$) at pH 7.1–7.2. A DNA:calcium complex is allowed to form at room temperature for up to a minute or more. The DNA:calcium complex thus formed is added to cells.

B. Strontium Phosphate

Approximately 10–40 µg of DNA is added to 1.2 mLs of 0.2 M of SrCl followed by the addition of an equal volume of 2×HBS (280 mM NaCl, 50 mM Hepes, 1.5 mM $Na_2PO_4$) at pH 7.5–8.0. A DNA-strontium complex is allowed to form at 37° C. for 30–100 minute. The DNA:strontium complex thus formed is added to cells.

C. Superfect

DNA is added to 100–700 µl of serum-free DMEM medium. Approximately 22.5 times (w/w) of 3 mg/ml Superfect, (QIAGEN®, (Valencia, Calif.) Cat. No. 301305) is added to the solution. A DNA:Superfect complex is allowed to form at room temperature for between about 2 minutes and about 30 minutes. The DNA: Superfect complex thus formed is added to the cells.

D. Polyethyleneimine (PEI)

DNA is added to 100–700 µl of serum-free DMEM medium. Approximately 2.25 times (w/w) of PEI is added to the solution. A DNA:Superfect complex is allowed to form at room temperature for between about 2 and about 30 minutes. The DNA:PEI complex thus formed is added to the cells.

Transfection Protocol

Suspension Cultures 0.6–1×10^7 cells are incubated in 2–3 mLs of S-medium containing various amounts of fetal calf serum in 50 mL conical tubes at 37° C., 5% $CO_2$ and 95% humidity. In a separate tube, Pladeno-5, pHelp 19 and pAAVLacZ were mixed with a transfection reagent and allowed to complex for a predetermined time. The DNA-transfection reagent complex is then added to the cells and gently mixed.

Cells mixed with the DNA-transfection reagent complex are incubated for approximately 3–4 hours. Following incubation, the cells are optionally shocked with glycerol, dimethylsulfoxide (DMSO) or a polysaccharide e.g., maltose. Shocking times can vary from about 1 minute to about 72 hours.

Following the shock, cells are diluted with approximately 5–10 volumes of S-medium. The diluted cells are placed in spinner flasks and incubated at 50–100 rpm for between about 40 hours and about 120 hours at 37° C. in a 5% $CO_2$ atmosphere.

After rAAV viral production is complete, e.g., after about 72 hours of incubation, cells are harvested and lysed by three successive rounds of freezing and thawing. A freeze/thaw lysate is prepared by freezing and thawing the cell suspension 3 times by alternating between a dry ice/ethanol bath (until the cells are completely frozen) and a 37° C. water bath (until completely thawed). Tissue debris is removed by centrifugation at 10,000×g for 10 minutes. The supernatant is collected and transferred to a sterile cryo-vial. Optionally, the adenovirus is heat inactivated by incubating the freeze/thaw lysate at 56° C. for 1 hour by submersion in a water bath. Any precipitate that forms during the heat inactivation is removed by centrifuging the sample at 10,000×g for 10 minutes. The supernatant containing AAV vector particles is then harvested.

The supernatant is titered for rAAV viral production either by dot blot to calculate the number of viral genomes or by transducing cells with the rAAV thus produced and harvested, and assaying for β-galactosidase activity to determine functional units. Transducing vector titers can be determined by infecting 293 cells, or any cell competent for transfection with AAV, with a dilution series of the rAAV virions. After 24 hours, the cells are fixed and stained with X-Gal. Sanes et al. (1986) *EMBO* 5:3133–3142. The titer is calculated by quantifying the number of blue cells.

Alternatively, the particles can be stored frozen at –70° C.

2. Suspension Cultures Adhered to Fibrous Disks

The cells adhering to the disks were transfected with AAV LacZ production plasmids by the calcium phosphate method described above. Briefly, 10 µg each of pladeno5, pHLP19, and pVlacZ, were added to 1 ml of 300 mM $CaCl_2$. This solution was rapidly mixed with 1 ml of 2×HBS (50 mM HEPES, 150 mM NaCl, 1.5 mM Phosphate pH 7.1) and the resulting 2 ml suspension was added to the culture dish containing the disks. The disks were incubated with the transfection medium for 8 hours with gentle agitation hourly. Three disks were fixed and stained 24 hours post transfection and the rest of the culture was harvested at 72 hours. The 72 cultures were subjected to freeze/thaw lysis and the resulting cleared supernatants were titered, as described above, for AAV LacZ functional units on 293 cells in the presence of adenovirus.

EXAMPLE 1

Transfection Using Calcium Phosphate as the Transfection Agent

Tissue culture 293-S cells were grown in 500 mL spinner flasks in 250 mLs of S-medium. Cells were centrifuged at 2000 rpm and 0.65×10^7 cells were incubated in 2–3 mLs of S-medium containing 0.1% Pluronic F-68 in a 50 mL conical tube at 50 rpm.

In a separate tube, a total of 36 µg of DNA (12 µg of Pladeno-5, 12 µg pHelp 19, and 12 µg pAAVLacZ) was added to 1.2 mLs of 0.3 M of $CaCl_2$ followed by the addition of an equal volume of 2×HBS (280 mM NaCl, 50 mM Hepes, 1.5 mM $Na_2PO_4$) at pH 7.1–7.2. The DNA:calcium complex was allowed to form at room temperature for 1 minute. The complex was then added to cells and gently mixed. At 3 hours, the cells were shocked with 10% glycerol for 1 minute, diluted with 30 mLs of S-medium and incubated for 72 hours.

After rAAV viral production was complete, cells were harvested and lysed by three successive rounds of freezing and thawing as described in the '856 patent, supra. Cells were pelleted and the supernatant was titered for rAAV viral production by assaying for β-galactosidase activity to determine functional units as described in the ×856 patent, supra. This transfection reagent gave a titer of $3.7×10^5$ functional units/mL or about $1.2×10^8$ genomes/mL.

EXAMPLE 2

Transfection Using Strontium Phosphate as the Transfection Agent

Tissue culture 293-S cells were grown in 50 mL conical tubes in S-medium containing either 5% or 50% fetal calf serum (FCS) at 50 rpm to a density of $0.65×10^7$. Once at the desired density, the cells were centrifuged and resuspended as described above in Example 1.

In a separate tube, a total of 22.5 µg of DNA (7.5 µg of Pladeno-5, 7.5 µg pHelp 19, and 7.5 µg pvLacZ) was added to 1.2 mLs of 0.3 M of $CaCl_2$ followed by the addition of an equal volume of 2×HBS (280 mM NaCl, 50 mM Hepes, 1.5 mM $Na_2PO_4$) at pH 7.1–7.2. The DNA:Ca complex was allowed to form at room temperature for 1 minute, added to cells, and mixed gently. At 3 hours, the cells were shocked with 10% glycerol for 1 minute and diluted with 30 mLs of S-medium.

After rAAV viral production was complete, cells were harvested and lysed as described above in Example 1. This transfection reagent gave a titer of $1.9×10^5$ functional units/mL or about $6.2×10^7$ genomes/mL in 5% FCS and a titer of $2.8×10^5$ functional units/mL or about $9×10^8$ genomes/mL in 5% FCS.

EXAMPLE 3

Transfection Using Superfect as the Transfection Agent

Four groups of 293-S cells were grown in 500 mL spinner flasks in 250 mLs of S-medium. Cells were centrifuged at 2000 rpm and $0.65×10^7$ cells were incubated in 2–3 mLs of S-medium containing 0.1% Pluronic F-68 in a 50 mL conical tube at 50 rpm.

In a separate tube, a total of 9 µg of DNA (3 µg of Pladeno-5, 3 µg pHelp 19, and 3 µg pvLacZ) was added to 100–700 µl of serum-free DMEM medium. Approximately 22.5 times (w/w) or about 202 µg of 3 mg/ml Superfect was added to the DNA, the DNA:Superfect was allowed to form at room temperature for 10 minutes. The complex was then added to cells and gently mixed. After a three-hour incubation period, the cells were shocked with 10% glycerol for 1 or 5 minutes diluted by addition of 30 mLs of S-medium and reincubated for about 72 hours.

After rAAV viral production was complete, cells were harvested and lysed as described above in Example 1. The titers are shown below in Table 1.

TABLE 1

| Tube | Pluronic | Glycerol Shock (minutes) | AAV Titer (functional units/mL) | AAV Titer (genomes/mL) |
|---|---|---|---|---|
| 1 | Yes | 1 | $2.5 × 10^6$/mL | $~8 × 10^8$/mL |
| 2 | No | 1 | $4 × 10^6$/mL | $~1.3 × 10^9$/mL |
| 3 | Yes | 5 | $2.4 × 10^7$/mL | $~8 × 10^8$/mL |

EXAMPLE 4

Transfection Using Polyethyleneimine as the Transfection Agent

Effect of DNA Concentration

This experiment was done to determine the effect of the added DNA concentration on the production of rAAV virions. In this experiment, 293-S cells were transfected with polyethyleneimine (PEI) and various amounts of DNA. The transfection was performed under the conditions described in Example 1, with the exception that a total of 9 µg of DNA ((3 µg of Pladeno-5, 3 µg pHelp 19, and 3 µg pvLacZ). The titers are shown below in Table 2.

TABLE 2

| Tube | PEI:DNA Ratio (w/w) | Glycerol Shock (minutes) | AAV Titer (functional units/mL) | AAV Titer (genomes/mL) |
|---|---|---|---|---|
| 1 | 3:1 | 3 | $2.8 × 10^6$/mL | $~9 × 10^8$/mL |
| 2 | 3:1 | — | $1.5 × 10^5$/mL | $~4.8 × 10^7$/mL |
| 3 | 6:1 | 3 | $4.8 × 10^6$/mL | $~1.6 × 10^9$/mL |
| 4 | 6:1 | — | $2.4 × 10^6$/mL | $~8 × 10^8$/mL |
| 5 | 9:1 | 3 | $4 × 10^5$/mL | $~1.3 × 10^8$/mL |
| 6 | 15:1 | 3 | $1.2 × 10^6$/mL | $~3.9 × 10^8$/mL |

EXAMPLE 5

Transfection Using Polyethyleneimine as the Transfection Agent

Effect of Glycerol Concentration

The following experiment was carried out to assess the effect of glycerol concentration and serum on transfection efficiency. The experiment was carried out as described in Example 1 above, with the exception that a total of 12 µg of DNA (4 µg of Pladeno-5, 4 µg pHelp 19, and 4 µg pvLacZ) was used. All glycerol shocks were done for 1 minute. The titers are shown below in Table 3.

TABLE 3

| Tube | PEI:DNA Ratio (w/w) | Glycerol (%) | Serum (%) | AAV Titer (functional units/mL) | AAV Titer (genomes/mL) |
|---|---|---|---|---|---|
| 1 | 1.5:1 | 10 | 5 | $9 × 10^5$/mL | $~3 × 10^8$/mL |
| 2 | 1.5:1 | 20 | 5 | $1.1 × 10^6$/mL | $~3.6 × 10^8$/mL |
| 3 | 1.5:1 | 10 | 0 | $7.2 × 10^5$/mL | $~2.3 × 10^8$/mL |
| 4 | 1.5:1 | 20 | 0 | $4.2 × 10^5$/mL | $~1.4 × 10^8$/mL |
| 5 | 2.5:1 | 10 | 5 | $3.7 × 10^6$/mL | $~1.2 × 10^9$/mL |
| 6 | 2.5:1 | 20 | 5 | $6.2 × 10^6$/mL | $~2 × 10^9$/mL |

EXAMPLE 6

Transfection Using Polyethyleneimine as the Transfection Agent

Effect of Complex Time and Shocking Agent

The following experiment was carried out to assess the transfection efficiency of PEI with various PEI-DNA complex time and shocking agent and concentration. The concentration of the shocking agents was 20%. The experiment was carried out as described in Example 5 above. A total of 12 μg of DNA (4 μg of Pladeno-5, 4 μg pHelp 19, and 4 μg pvLacZ) was used. The titers are shown below in Table 4.

TABLE 4

| Tube | PEI:DNA Ratio (w/w) | PEI:DNA Complex Time (min.) | DNA | Shocking Agent | Shock Time (min) | AAV Titer (average functional units/mL) | AAV Titer (average genomes/mL) |
|---|---|---|---|---|---|---|---|
| 1 | 2.25:1 | 10 | 12 | Glycerol | 1 | $6.1 \times 10^6$/mL | $\sim 2 \times 10^9$/mL |
| 2 | 2.25:1 | 10 | 12 | Maltose | 5 | $3.2 \times 10^6$/mL | $\sim 1 \times 10^9$/mL |
| 3 | 2.25:1 | 3 | 12 | Glycerol | 1 | $7.2 \times 10^6$/mL | $\sim 2.3 \times 10^9$/mL |
| 4 | 2.25:1 | 6 | 12 | Glycerol | 1 | $1.5 \times 10^7$/mL | $\sim 4.9 \times 10^9$/mL |
| 5 | 2.25:1 | 10 | 12 | Glycerol | 3 | $1.3 \times 10^7$/mL | $\sim 4.2 \times 10^9$/mL |
| 6 | 1.12:1 | 10 | 24 | Glycerol | 1 | $1.0 \times 10^7$/mL | $\sim 3.3 \times 10^9$/mL |
| 7 | 3:1 | 10 | 12 | Glycerol | 1 | $1.9 \times 10^7$/mL | $\sim 6 \times 10^9$/mL |

Accordingly, novel methods for producing recombinant AAV virions have been disclosed. Although preferred embodiments of the subject invention have been described in some detail, it is understood that obvious variations can be made without departing from the spirit and the scope of the invention as defined by the appended claims.

EXAMPLE 7

Transfection of Suspension Cells Adhered to Fibrous Disks Using Calcium Phosphate Method 293-S cells adhered to fibrous disks as described above were transfected with AAV LacZ plasmids by calcium phosphate transfection, as described above. Briefly, 10 μg each of pladeno5, pHLP19, and pVlacZ, were added to 1 l of 300 MM CaCl$_2$. This solution was rapidly mixed with 1 ml of 2×HBS (50 mM HEPES, 150 mM NaCl, 1.5 mM Phosphate pH 7.1) and the resulting 2 ml suspension was added to the culture dish containing the disks. The disks were incubated with the transfection medium for 8 hours with gentle agitation hourly. Three disks were fixed and stained 24 hours post transfection and the rest of the culture was harvested at 72 hours. The 72 cultures were subjected to freeze/thaw lysis and the resulting cleared supernatants were titered for AAV LacZ functional units on 293 cells in the presence of adenovirus.

Microscopy

Non-transfected cells we not easily visualized on the disks but transfected cells expressing beta-galactosidase and stained with X-gal were easily seen (vector producing cells express the beta-galactosidase transgene). The number of transfected cells increased with cell loading time but the disks seemed no more than approximately 25% loaded (e.g. 75% of the disk surface area was free of cells) even after 2 hours of incubation with the cells in the spinner flask. Most of the discernable cells seemed to be transfected.

TABLE 5

| Cell loading time | Disks assayed | Total functional units | Functional units/disk |
|---|---|---|---|
| 15 min. | 8 | $4 \times 10^6$ | $5 \times 10^5$ |
| 30 min. | 18 | $8 \times 10^6$ | $4.4 \times 10^5$ |
| 60 min. | 18 | $7.5 \times 10^6$ | $4.1 \times 10^5$ |
| 120 min. | 15 | $1.5 \times 10^7$ | $1 \times 10^6$ |

Thus, a packed bed reactor contains approximately 35 gm of fibrous disks or 6480 disks per liter of bed. The AAV vector production per liter can be calculated to be $6.5 \times 10^9$ functional units per liter (data from the 120 min. cell loading time).

EXAMPLE 8

Large Scale Production of rAAV Virions in Suspension Cell Cultures Adhered to Fibrous Disks Cells sufficient to occupy approximately 10–20% of the surface area of the fibrous disks in a packed bed reactor are grown in suspension culture, in calcium-free media, in the absence of disks. These cells are loaded on to the fibrous-disk matrix such that they are entrapped in the disk. The seeded bed is then be perfused with calcium containing media to induce the cells to attach to the fibrous disk matrix. Seeding the bed in the absence of calcium should prevent cell aggregation and permit uniform dispersal of the cells. Aggregated cells that are not uniformly dispersed transfect poorly and do not efficiently produce AAV vector. The attached cells are grown for 48 hours before the are transfected with AAV vector production plasmids. The AAV vector are harvested 72 hours later by lysis of the cells in situ. This can be accomplished by several means (freeze/thaw lysis, chemical lysis, inclusion of the adenovirus lysis genes along with the transfected production plasmids). The AAV vector released into the culture media will then be collected and concentrated by ultrafiltration prior to purification.

EXAMPLE 9

Large Scale Production of rAAV Virions in Adherent Cell Culture Systems

To evaluate recombinant AAV virion production in roller bottles, expanded roller bottles and T-225 flasks the experiments shown in Table 6 were performed.

TABLE 6

| Experiment Number | Type of Culture Container | Seeding Density |
|---|---|---|
| 298-1A | Roller Bottle (850 cm$^2$) | $2.5 \times 10^6$ equivalent |
| 298-1B | Roller Bottle (850 cm$^2$) | $1.5 \times 10^6$ equivalent |
| 296-8A | Roller Bottle (850 cm$^2$) | $3 \times 10^6$ equivalent |
| 296-8B | Expanded Roller Bottle (1700 cm$^2$) | $3 \times 10^6$ equivalent |
| 296-8C | T-225 flask | $3 \times 10^6$ equivalent |
| 296-8D | Triple flask | $3 \times 10^6$ equivalent |
| 296-8E | T-225 flask | $2.5 \times 10^6$ equivalent |
| 296-8F | T-225 flask | $1.5 \times 10^6$ equivalent |

All cultures were transfected 4 days after seeding using the calcium phosphate transfection method described above.

Virions were isolated and titers calculated as described above. The results shown in Table 7 demonstrate substantially improved virion production as compared to standard protocols. Only Experiments 298-1B, 296-8A and 296-8D gave dot blot results within range.

TABLE 7

| Sample | Cell Density | Particle/mL | Trans. units/mL | Vol. | Tot. vg* | Tot. TU# | vg/cm²** | TU/cm² | vg/TU |
|---|---|---|---|---|---|---|---|---|---|
| Roller Bottle 298-1A | $6.7 \times 10^3$ cells/cm² | $1.30 \times 10^{10}$ | $3.90 \times 10^7$ | 4 | $5.20 \times 10^{10}$ | $1.56 \times 10^8$ | $6.12 \times 10^7$ | $1.84 \times 10^5$ | $3.33 \times 10^2$ |
| Roller Bottle 298-1B | $1.1 \times 10^4$ cells/cm² | $7.00 \times 10^{10}$ | $1.30 \times 10^8$ | 4 | $2.80 \times 10^{11}$ | $5.20 \times 10^8$ | $3.29 \times 10^8$ | $6.12 \times 10^5$ | $5.38 \times 10^2$ |
| Roller Bottle 296-8A | $1.3 \times 10^4$ cells/cm² | $1.70 \times 10^{11}$ | $5.00 \times 10^7$ | 5 | $8.50 \times 10^{11}$ | $2.50 \times 10^8$ | $1.00 \times 10^9$ | $2.94 \times 10^5$ | $3.40 \times 10^3$ |
| Exp Roller Bottle 296-8B | $1.3 \times 10^4$ cells/cm² | $2.00 \times 10^9$ | $7.30 \times 10^6$ | 10 | $2.00 \times 10^{10}$ | $7.30 \times 10^7$ | $1.18 \times 10^7$ | $4.29 \times 10^4$ | $2.74 \times 10^2$ |
| T225, $3 \times 10^6$ cells 296-8C | $1.3 \times 10^4$ cells/cm² | $1.00 \times 10^{10}$ | $1.20 \times 10^7$ | 2 | $2.00 \times 10^{10}$ | $2.40 \times 10^7$ | $8.89 \times 10^7$ | $1.07 \times 10^5$ | $8.33 \times 10^2$ |
| Triple Flask 296-8D | $1.3 \times 10^4$ cells/cm² | $1.90 \times 10^{11}$ | $4.30 \times 10^7$ | 3 | $5.70 \times 10^{11}$ | $1.29 \times 10^8$ | $1.14 \times 10^9$ | $2.58 \times 10^5$ | $4.42 \times 10^3$ |
| T-225, $2.5 \times 10^6$ cells 296-8E | $1.1 \times 10^4$ cells/cm² | $4.30 \times 10^9$ | $1.10 \times 10^7$ | 2 | $8.60 \times 10^9$ | $2.20 \times 10^7$ | $3.82 \times 10^7$ | $9.78 \times 10^4$ | $3.91 \times 10^2$ |
| T-225, $1.5 \times 10^6$ cells 296-8F | $6.7 \times 10^4$ cells/cm² | $1.00 \times 10^{10}$ | $1.90 \times 10^7$ | 2 | $2.00 \times 10^{10}$ | $3.80 \times 10^7$ | $8.89 \times 10^7$ | $1.69 \times 10^5$ | $5.26 \times 10^2$ |

*"vg" refers to total virion genomes;
"TU" refers to transducing units.

We claim:

1. A method of producing large-scale quantities of recombinant adeno-associated virus (AAV) virions, comprising:
   a) growing a population of cells in at least one roller bottle while rotating said roller bottle;
   b) transfecting said cells in said roller bottle while rotating said roller bottle with at least one polynucleotide molecule comprising an AAV helper construct and an AAV expression vector;
   c) infecting said cells with an AAV helper virus while rotating said roller bottle;
   d) culturing the transfected cells while rotating said roller bottle under conditions that permit the production of said rAAV virions; and
   e) harvesting said rAAV virions.

2. The method of claim 1, wherein said cells are transfected using calcium phosphate precipitation.

3. The method of claim 1, wherein said roller bottle is an expanded roller bottle.

4. A method of producing large-scale quantities of recombinant adeno-associated virus (AAV) virions, comprising:
   a) growing a population of cells in at least one roller bottle while rotating said roller bottle;
   b) transfecting said cells in said roller bottle while rotating said roller bottle with at least two polynucleotide molecules comprising an AAV helper construct, an accessory function vector, and an AAV expression vector,
   c) culturing the transfected cells while rotating said roller bottle under conditions that permit the production of said rAAV virons; and
   d) harvesting said rAAV virions.

5. The method of claim 4, wherein said cells are transfected with at least three polynucleotide molecules comprising an AAV helper construct, an accessory function vector, and an AAV expression vector.

6. The method of claim 5, wherein said cells are transfected using calcium phosphate precipitation.

7. The method of claim 4, wherein said cells are transfected using calcium phosphate precipitation.

8. The method of claim 4, wherein said roller bottle is an expanded roller bottle.

* * * * *